United States Patent [19]

Iwai et al.

[11] Patent Number: 4,665,029

[45] Date of Patent: May 12, 1987

[54] HEAT-RESISTANT LIPASE

[75] Inventors: Mieko Iwai, 3-1, Takanodai 5-chome, Suita, Osaka; Yoshio Tominaga, 7-2, Utajima 2-chome, Nishiyodogawa-ku, Osaka, Osaka; Katsumi Nakanishi, Osaka, all of Japan

[73] Assignees: Daikin Kogyo Co., Ltd.; Mieko Iwai; Yoshio Tominaga, all of Osaka, Japan

[21] Appl. No.: 583,188

[22] Filed: Feb. 24, 1984

[30] Foreign Application Priority Data

Feb. 25, 1983 [JP] Japan .................................. 58-31388

[51] Int. Cl.$^4$ ......................... C12N 9/20; C12N 1/14; C12R 1/845
[52] U.S. Cl. ................................... 435/198; 435/254; 435/939
[58] Field of Search ........................ 435/198, 254, 939

[56] References Cited

U.S. PATENT DOCUMENTS 3,898,133  8/1975  Craveri et al. ..................... 435/198
4,283,494  8/1981  Kokusho et al. .................. 435/198

FOREIGN PATENT DOCUMENTS 0063087  4/1982  Japan ................................. 435/198

OTHER PUBLICATIONS

Iwai et al., "The Purification and the Properties of Three Kinds of Lipases from *Rhizopus Delemer*", *Agr. Biol. Chem.*, V. 38, No. 6, 1974, pp. 1241–1247.

Primary Examiner—Thomas G. Wiseman
Assistant Examiner—Elizabeth C. Weimar
Attorney, Agent, or Firm—Birch, Stewart, Kolasch and Birch

[57]  ABSTRACT

A novel lipase characterized in that at least 95% of its original activity is maintained after being treated at a temperature of 30° to 80° C. for 15 minutes, which may be produced by cultivating *Rhizopus chinensis* FERM BP-936 in a culture medium and recovering the produced enzyme from the medium.

12 Claims, 5 Drawing Figures

HEAT-RESISTANT LIPASE

FIELD OF THE INVENTION

This invention relates to a heat-resistant lipase. More particularly, it relates to a novel lipase having such heat-resistance that its activity is maintained after being heated at a temperature higher than 50° C. and having good stability in a wide pH range.

BACKGROUND OF THE INVENTION

Lipase is an enzyme which decomposes fat and fatty acid esters and is extracted from internal organs of animals or produced by cultivating microorganisms. However, conventional lipase is unstable at a high temperature, especially at a temperature higher than 50° C. and stable only in a narrow pH range. Therefore, it is not suitable for industrial use.

For example, Japanese Patent Publication No. 42266/1981 discloses a process for production of lipase which comprises cultivating Rhizopus chinensis HI-S in a culture medium and recovering lipase from the culture. Lipase obtained by this process, however, loses its activity at a temperature higher than 50° C. and is stable only in a pH range of 4.0 to 8.0.

As a result of the extensive study, it has now been found that a certain specific strain belonging to the genus Rhizopus produces lipase having improved heat-resistance and pH stability.

SUMMARY OF THE INVENTION

According to the present invention, there is provided a novel lipase characterized in that at least 95%, preferably 100% of its original activity is maintained after being heated at a temperature of 30° to 80° C. for 15 minutes.

Preferably, the lipase of the invention maintains at least 90%, preferably at least 95%, more preferably 100% of its original activity after being heated at 80° C. for 60 minutes, and at least 75%, preferably at least 80%, more preferably at least 85% or its original activity after being heated at 80° C. for 120 minutes. Further, it maintains at least 55%, preferably at least 60%, more preferably at least 65% of its original activity after being heated at 90° C. for 60 minutes, and at least 30%, preferably at least 35%, more preferably 40% of its original activity after being heated at 90° C. for 120 minutes.

DETAILED DESCRIPTION OF THE INVENTION

Lipase of the invention may be produced by cultivating, for example, a known strain Rhizopus chinensis IFO 4745 in an appropriate culture medium. Rhizopus chinensis IFO 4745 was originally deposited at Culture Collection of the Institute for Fermentation (IFO) of 4-54 Juso-nishino-cho, Higashi Yodogawa-ku, Osaka, Japan but is no longer available at that site. However, the microorganism is now available in the Fermentation Research Institute Agency of Industrial Science and Technology at 1-3, Higashi 1 Chome Yatabe-machi Tsukuba-gun Ibaraki-ken 305, Japan, Deposit No. FERM BP-936. The microorganisms deposited as FERM BP-936 are identical to the microorganisms previously identified as Strain IFO 4745.

The strain may be cultivated in a liquid or solid culture medium by static culture, shaking culture or submerged culture under aeration, and preferably in the liquid medium by shaking the culture or submerging the culture under aeration.

The culture medium contains carbon sources which can be utilized by the strain (eg. glucose, sucrose, mannitol, dextrin, cellulose, starch, glycerin, sorbitol, wheat bran, rice bran, etc.), nitrogen sources which can be utilized by the strain (eg. pepton, meat extract, yeast extract, dry yeast, soy bean powder, soy bean dreg, casein, gluten, Casamino acid, corn steep liquor, ammonium salts such as ammonium sulfate and ammonium nitrate, etc.) and various inorganic salts (eg. phosphates, fulfates, chlorides, etc.). In addition to these materials, vitamins and nucleic acid may be added to the culture medium.

The strain is preferably precultivated in the same culture medium as used in its cultivation.

The cultivation temperature is usually from 20° to 40° C., preferably from 25° to 35° C., and cultivation time is usually from 2 to 10 days, preferably form 3 to 7 days. The culture medium is preferably neutral or slightly acid. When the medium is aerated, the aeration rate is 0.5 to 1 l/min. per liter of the medium.

When the liquid medium is used, the produced heat-resistant lipase is mainly accumulated in the medium. The strain is removed from the medium by filtration or centrifugation of the medium and the produced lipase is collected and purified by a per se conventional method, for example, salting out with inorganic salts (eg. ammonium sulfate, sodium sulfate, sodium chloride, etc.), fractional precipitation with organic solvents (eg. alcohols such as methanol and ethanol, acetone, etc.), absorption and desorption by ion exchange resins (eg. Sephadex (trade mark), etc.), chromatography, molecular sieve method, precipitation with proteinaceous precipitators (eg. nucleic acid, tannin, phosphorus wolframates, etc.), precipitation at isoelectric point, dialysis, electrophresis, etc.

The heat-resistant lipase of the invention has the following characteristics:

1. PH Stability

Figure 1:
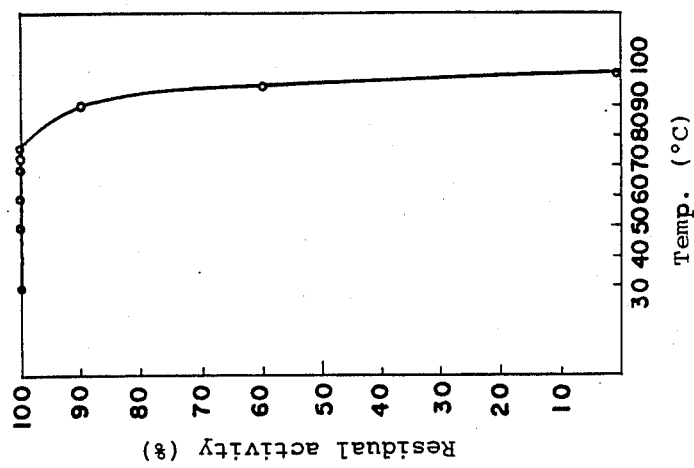
FIG. 1 shows the residual activity of the lipase of the invention vs. pH.

It keeps 100% of the original activity in a wide pH range of from 2.5 to 11 (cf. Table 1 and FIG. 1).

2. Heat-resistance

Figure 2:
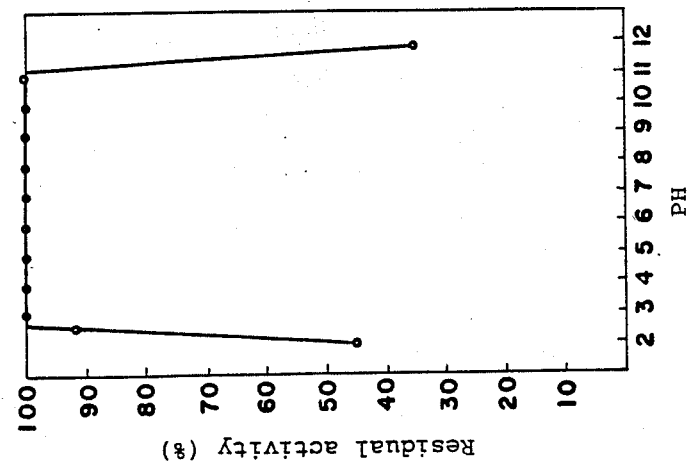
FIG. 2 shows the residual activity of the lipase of the invention vs. temperature.
Figure 3:
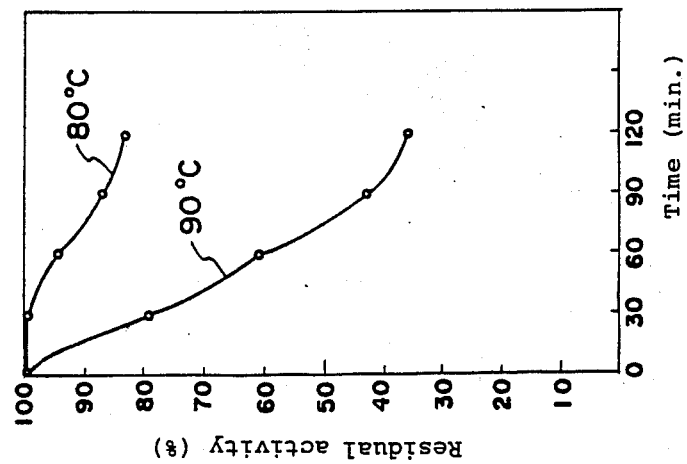
FIG. 3 shows the residual activity of the lipase of the invention at 80° C. and 90° C.

It keeps 100% of the original activity after being heated at 75° C. for 15 minutes, 80% after being heated at 80° C. for 120 minutes and 60% after being heated at 90° C. for 60 minutes (cf. Tables 2 and 3 and FIGS. 2 and 3).

3. Optimum pH Condition

Figure 4:
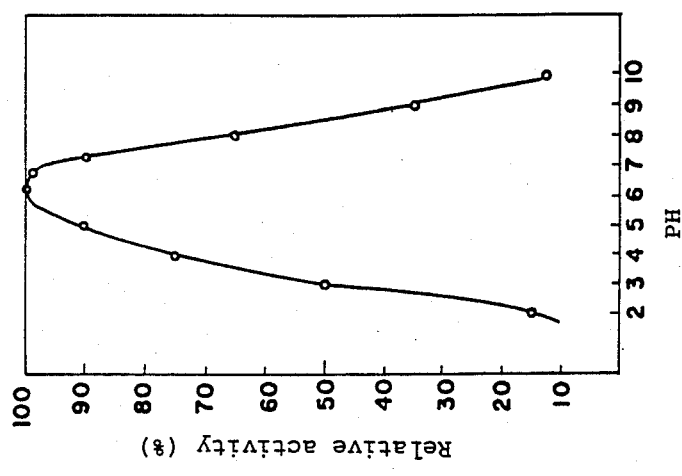
FIG. 4 shows the optimum pH condition for the lipase of the invention.

The optimum pH condition for the heat-resistant lipase of the invention is from 6.5 to 7.0 (cf. FIG. 4).

4. Optimum Temperature Condition

Figure 5:
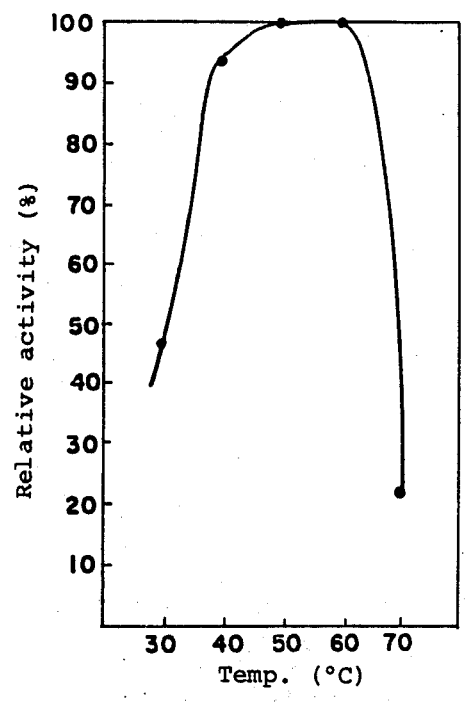
FIG. 5 shows the optimum temperature condition for the lipase of the invention.

The optimum temperature condition for the heat-resistant lipase of the invention is from 40° to 60° C. (cf. FIG. 5).

5. Position Specificity against Triglyceride

The lipase of the invention cleaves the ester bondings at 1- and 3-positions but not that at 2-position.

6. Fatty Acid Specificity against Esters of Triglyceride with Single Acid

When the enzymatic activity against triolein is taken for 100, relative enzymatic activities against some other esters of triglyceride with a single acid are as follows:

Triacetin—0
Tripropion—10
Tributyrin—65
Tricaproin—64
Tricaprylin—55
Tricaprin—154
Trilaurin—89
Trimyristin—5
Tripalmitin—13
Tristearin—3

7. Isoelectric Point

According to the isoelectric electrophoresis method, the isoelectric point of the lipase of the invention is 9.2.

8. Molecular Weight

Molecular weight of the lipase of the invention is 30,000 according to SDS electrophoresis.

The above characteristics are measured as follows:

(a) Activity of the Lipase of the Invention

In a glass vessel having an inner diameter of 4.4 cm and a height of 8.2 cm, a reaction medium containing olive oil (1 g) and a combination of M/20 acetic acid buffer (pH 5.6) and M/100 $CaCl_2$ (5 ml) and an enzyme solution diluted to a predetermined concentration (0.05 to 1 ml) were reacted at 30° C. for one hour with stirring at 500 rpm. Then, the reaction was terminated by the addition of ethanol (20 ml).

The titer of the enzyme was determined by titrating the liberated fatty acid with N/20 potassium hydroxide, the end point being pH 10. One unit of the enzyme is an amount which liberates one microequivalent of fatty acid per minute.

(b) Measurement of pH Stability

An enzyme solution was added in glycine-hydrochloric acid buffer at pH of 2 to 4, in McIlvaine buffer at pH of 4 to 7 or in glycine-sodium hydroxide at pH of 7 to 12 and kept at 30° C. for 15 hours. Residual activities were measured in the same manner as in the above (a). The results are shown in Table 1 and FIG. 1.

TABLE 1

| pH | Residual activity (%) |
|---|---|
| 2.0 | 45 |
| 2.5 | 100 |
| 11 | |
| 12 | 35 |

(c) Measurement of Optimum pH Condition

In a mixture of olive oil (1 g) and McIlvaine buffer (5 ml), an enzyme solution (0.5 ml) was added and reacted at 30° C. for 60 minutes with stirring at 500 rpm. The maximum activity was taken as 100% and the relative activity was then calculated.

(d) Measurement of Temperature Stability

An enzyme solution was kept at 30°, 50°, 60°, 70°, 75°, 80°, 90°, 95° or 100° C. for 15 minutes and cooled with ice for 5 minutes. Residual activities were measured in the same manner as in the above (a). The results are shown in FIG. 2 and Table 2.

TABLE 2

| Temp. (°C.) | Residual activity (%) |
|---|---|
| 30 | 100 |
| 80 | |
| 90 | 90 |
| 95 | 60 |
| 100 | 0 |

Alternatively, the enzyme solution was kept at 80° C. or 90° C. for 0, 30, 60, 90 and 120 minutes and cooled with ice for 5 minutes. Residual activities were measured in the same manner as in the above (a). The results are shown in Table 3 and FIG. 3.

TABLE 3

| Temp. (°C.) | Time (min.) | Residual activity (%) |
|---|---|---|
| 80 | 30 | 100 |
| | 60 | 95 |
| | 90 | 85 |
| | 120 | 80 |
| 90 | 30 | 80 |
| | 60 | 60 |
| | 90 | 42 |
| | 120 | 35 |

(e) Measurement of Optimum Temperature

In a mixture of olive oil (1 g) and a combination of M/20 acetic acid buffer (pH 5.6) and M/100 $CaCl_2$ (5 ml), an enzyme solution was added and kept at a temperature of 30° to 80° C. for 60 minutes with stirring at 500 rpm. The maximum activity was taken as 100% and the relative activity was then calculated.

As discussed above, the lipase of the invention has excellent heat-resistance and good stability in a wide pH range and thus is commercially valuable. For example, oil can be manufactured at a high temperature, at which the flowability of the oil is better and the reaction is accelerated. The lipase of the invention is useful as an enzyme for detergent and digestion.

PREFERRED EMBODIMENT OF THE INVENTION

The present invention will be hereinafter explained further in detail by the following Example.

EXAMPLE

A culture medium containing 5% of peptone, 2% of glucose, 0.1% of $NaNO_3$, 0.1% of $KH_2PO_4$, 0.05% of $MgSO_4.7H_2O$ was adjusted to pH of 6.0 and each 60 ml was charged in 50 Sakaguchi-type 500 ml flasks.. $10^5$ spores of *Rhizopus Chinensis* IFO 4745 per flask were inoculated in the flasks and cultivated for 27° C. for 96 hours with shaking to obtain filtered medium containing 40 units/ml of the enzyme.

In the filtrate, ammonium sulfate was added to 80% of saturation to salt out the enzyme. The thus obtained enzyme was purified by the use of SP-Sephadex (trade mark) C-50, Sephadex (trade mark) G-100 and isoelectric electrophoresis to produce a homogeneous lipase in the disk electrophoresis.

The specific activity of the obtained lipase was 3,000 units/mg.

What is claimed is:

1. An isolated lipase prepared by cultivating *Rhizopus chinensis* Ferm BP-936 in a culture medium and recovering the produced lipase from said medium, said lipase being characterized in that at least 90% of its original activity is maintained after said lipase is heated at a temperature of at least 80° C. for 60 minutes.

2. An isolated lipase according to claim 1, which maintains 100% of its original activity at a pH of from 2.5 to 11.

3. An isolated lipase according to claim 1, which has a molecular weight of 30,000 and an isoelectric point of 9.2.

4. An isolated lipase according to claim 1, which is position specific against triglycerides such that said lipase cleaves the ester bondings at 1- and 3-positions but not at 2-positions.

5. An isolated lipase according to claim 1, wherein 80% of its original activity is maintained after said lipase is heated at 80° C. for 120 minutes.

6. An isolated lipase having the following characteristics:
   (a) said lipase maintains at least 90% of its original activity after said lipase is heated at a temperature of at least 80° C. for 60 minutes; and
   (b) said lipase maintains 100% of its original activity at a pH of from 2.5 to 11.

7. An isolated lipase according to claim 6, which is position specific against triglycerides such that said lipase cleaves the ester bondings at 1- and 3-positions but not at 2-positions.

8. An isolated lipase according to claim 6, wherein 80% of its original activity is maintained after said lipase is heated at 80° C. for 120 minutes.

9. An isolated lipase according to claim 8, wherein said lipase has a molecular weight of 30,000.

10. An isolated lipase having the following characteristics:
    (a) said lipase maintains at least 90% of its original activity after said lipase is heated at a temperature of at least 80° C. for 60 minutes;
    (b) said lipase maintains 100% of its original activity at a pH of from 2.5 to 11;
    (c) a molecular weight of 30,000; and
    (d) an isoelectric point of 9.2.

11. An isolated lipase according to claim 10, which is position specific against triglycerides such that said lipase cleaves the ester bondings at 1- and 3-positions but not at 2-positions.

12. An isolated lipase according to claim 11, wherein 80% of its original activity is maintained after said lipase is heated at 80° C. for 120 minutes.

* * * * *